United States Patent
Huang et al.

(10) Patent No.: US 12,414,821 B2
(45) Date of Patent: Sep. 16, 2025

(54) SYSTEM AND METHOD FOR REGISTERING OPERATING IMAGES

(71) Applicant: METAL INDUSTRIES RESEARCH & DEVELOPMENT CENTRE, Kaohsiung (TW)

(72) Inventors: Bing-Feng Huang, Kaohsiung (TW); Jin-Yuan Syue, Tainan (TW); Hsiang-Hsiang Choo, Taipei (TW); Chih-Lung Lin, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 1151 days.

(21) Appl. No.: 17/128,230

(22) Filed: Dec. 21, 2020

(65) Prior Publication Data
US 2022/0192752 A1   Jun. 23, 2022

(51) Int. Cl.
| | |
|---|---|
| *A61B 34/20* | (2016.01) |
| *A61B 6/00* | (2006.01) |
| *A61B 6/12* | (2006.01) |
| *A61B 6/58* | (2024.01) |
| *G01T 1/161* | (2006.01) |

(Continued)

(52) U.S. Cl.
CPC ........... *A61B 34/20* (2016.02); *A61B 6/12* (2013.01); *A61B 6/4441* (2013.01); *A61B 6/5247* (2013.01); *A61B 6/583* (2013.01); *G01T 1/161* (2013.01); *G06F 18/25* (2023.01); *G06T 7/33* (2017.01); *G06V 10/10* (2022.01); *A61B 2034/2057* (2016.02); *G06T 2207/10116* (2013.01); *G06T 2207/30004* (2013.01); *G06T 2207/30196* (2013.01);

(Continued)

(58) Field of Classification Search
None
See application file for complete search history.

(56) References Cited

U.S. PATENT DOCUMENTS

| | | |
|---|---|---|
| 6,351,659 B1 | 2/2002 | Vilsmeier |
| 10,182,872 B2 | 1/2019 | Chang et al. |

(Continued)

FOREIGN PATENT DOCUMENTS

| | | |
|---|---|---|
| CN | 104000654 A | 8/2014 |
| CN | 104619254 A | 5/2015 |

(Continued)

*Primary Examiner* — Patricia J Park
(74) *Attorney, Agent, or Firm* — CKC & Partners Co., LLC

(57) ABSTRACT

A system for registering operating images includes an X-ray imaging machine, a visible-light camera, a rectifier and a computer system. The X-ray imaging machine captures a first X-ray image of the rectifier, and the visible-light camera captures a first visible-light image of the rectifier at the same time. The computer system recognizes the rectifier in the first X-ray image and in the first visible-light image to compute a conversion model between a coordinate system of the X-ray imager and a coordinate system of the visible-light camera. The X-ray imaging machine also captures a second X-ray image of a patient on which a positioning marker is set, and the visible-light camera captures a second visible-light image of the positioning marker. The computer system provides a navigation interface by combining the second X-ray image and the second visible-light image based on the conversion model.

7 Claims, 4 Drawing Sheets

(51) Int. Cl.
*G06F 18/25* (2023.01)
*G06T 7/33* (2017.01)
*G06V 10/10* (2022.01)
*H04N 23/54* (2023.01)

(52) U.S. Cl.
CPC *G06T 2207/30204* (2013.01); *G06V 2201/03* (2022.01); *H04N 23/54* (2023.01)

(56) References Cited

U.S. PATENT DOCUMENTS

| | | | |
|---|---|---|---|
| 10,512,451 | B2 | 12/2019 | Mahfouz |
| 2007/0270660 | A1 | 11/2007 | Caylor, III et al. |
| 2013/0066196 | A1 | 3/2013 | Graumann et al. |
| 2015/0257849 | A1* | 9/2015 | Barth ............... A61B 17/3403 600/424 |
| 2018/0092699 | A1 | 4/2018 | Finley |
| 2019/0000564 | A1* | 1/2019 | Navab ............... H04N 13/254 |
| 2021/0330273 | A1* | 10/2021 | Crawford ............. A61B 6/487 |
| 2024/0041558 | A1* | 2/2024 | Siewerdsen ........... A61B 90/94 |

FOREIGN PATENT DOCUMENTS

| | | | |
|---|---|---|---|
| TW | I572316 | B | 3/2017 |
| TW | I586327 | B | 6/2017 |
| TW | I605789 | B | 11/2017 |

\* cited by examiner

SYSTEM AND METHOD FOR REGISTERING OPERATING IMAGES

BACKGROUND

Field of Invention

The present disclosure relates to a system and a method for registering operating images.

Description of Related Art

With the increase of aging population and the influence of modern life characteristics such as obesity, sedentary, etc., diseases of spine lesions are increasing year by year. If conservative treatment fails, it is often necessary to rely on implants to reduce pain and maintain basic functions. The spine is responsible for protecting the central nervous system, but the portion where the implants that can be applied are quite narrow. For example, a pedicle screw may damage the central nervous system. Although an orthopedic minimally invasive surgery is available in the market, how to accurately track the position of the spine during the surgery is still an issue since the position of the spine changes with the patient's posture.

SUMMARY

Embodiments of the present disclosure provide a system for registering operating images. The system includes an X-ray imaging machine, a visible-light camera disposed on the X-ray imaging machine, a rectifier, and a computer system. The X-ray imaging machine is configured to capture a first X-ray image of the rectifier, and the visible-light camera is configured to capture a first visible-light image of the rectifier at the same time. The computer system is configured to recognize the rectifier in the first X-ray image and in the first visible-light image to compote a conversion model between a first coordinate system of the X-ray imaging machine and a second coordinate system of the visible-light camera. The X-ray imaging machine is further configured to capture a second X-ray image of a patient on which a positioning mark is set, and the visible-light camera is configured to capture a second visible-light image of the positioning mark. The computer system is configured to provide a navigation interface by combining the second X-ray image and the second visible-light image based on the conversion model.

In some embodiments, coordinates of the rectifier in the first coordinate system are represented as a vector X. Coordinates of the rectifier in the second coordinate system are represented as a vector Y. The computer system is configured to compute the conversion model according to the following equation (1), in which the conversion model is a matrix $T_{XM}$.

$$X = T_{XM} Y \quad (1)$$

In some embodiments, the rectifier includes multiple metal balls.

In some embodiments, the X-ray imaging machine is a C-arm X-ray machine which includes an emitting terminal and a receiving terminal. The visible-light camera is disposed on the receiving terminal.

In some embodiments, the system further includes a surgical instrument and an instrument camera which is fixed on the surgical instrument.

From another aspect, embodiments of the present disclosure provide a method for registering operating images for a computer system. The method including: capturing, by an X-ray imaging machine, a first X-ray image of a rectifier, and capturing, by a visible-light camera, a first visible-light image of the rectifier at same time, in which the visible-light camera is disposed on the X-ray imaging machine; recognizing the rectifier in the first X-ray image and in the first visible-light image to compote a conversion model between a first coordinate system of the X-ray imaging machine and a second coordinate system of the visible-light camera; capturing, by the X-ray imaging machine, a second X-ray image of a patient on which a positioning mark is set; capturing, by the visible-light camera, a second visible-light image of the positioning mark; and providing a navigation interface by combining the second X-ray image and the second visible-light image based on the conversion model.

In some embodiments, the method further includes computing the conversion model according to the equation (1).

In the system and the method, the system is simplified by disposing the visible-light camera on the X-ray imaging machine. A conversion model between the X-ray imaging machine and the visible-light camera is computed by using a rectifier. Therefore, the X-ray image and the visible-light image can be combined to provide a navigation interface.

BRIEF DESCRIPTION OF THE DRAWINGS

The invention can be more fully understood by reading the following detailed description of the embodiment, with reference made to the accompanying drawings as follows.

DETAILED DESCRIPTION

Specific embodiments of the present invention are further described in detail below with reference to the accompanying drawings, however, the embodiments described are not intended to limit the present invention and it is not intended for the description of operation to limit the order of implementation. Moreover, any device with equivalent functions that is produced from a structure formed by a recombination of elements shall fall within the scope of the present invention. Additionally, the drawings are only illustrative and are not drawn to actual size.

The using of "first", "second", "third", etc. in the specification should be understood for identifying units or data described by the same terminology, but are not referred to particular order or sequence.

Figure 1:
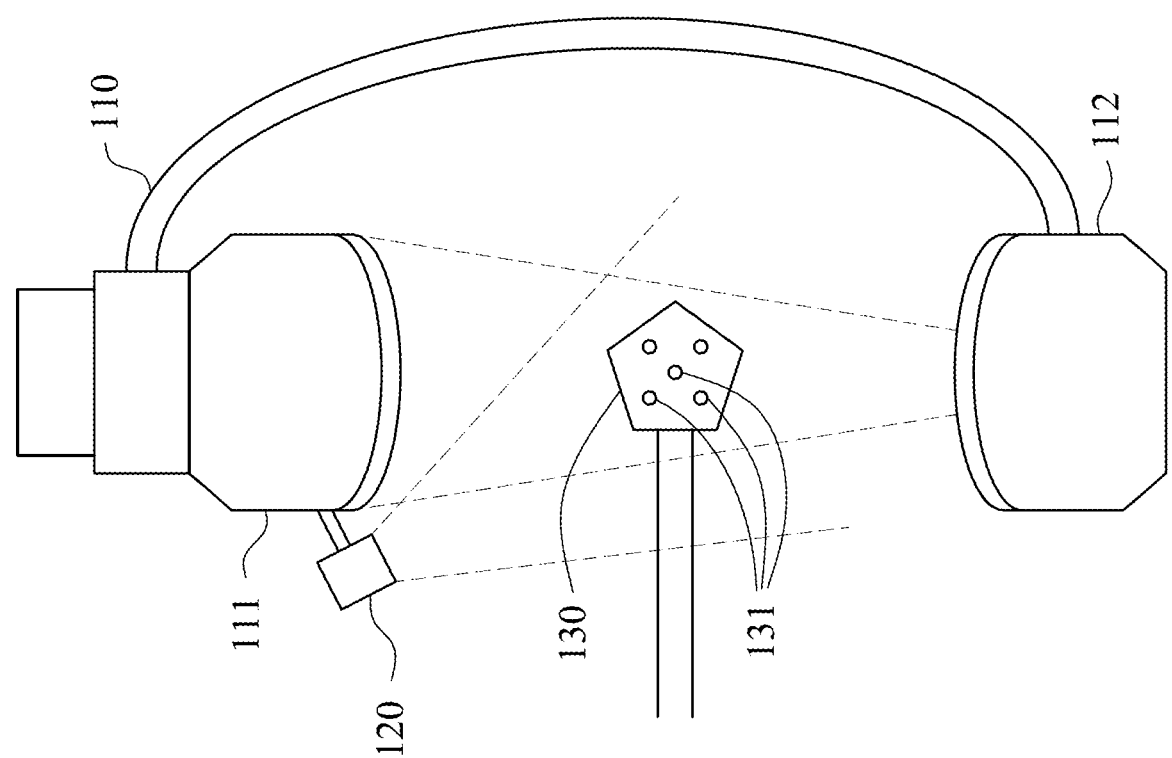
FIG. 1 is a schematic diagram of a system for registering operating images in accordance with an embodiment.
Figure 1:
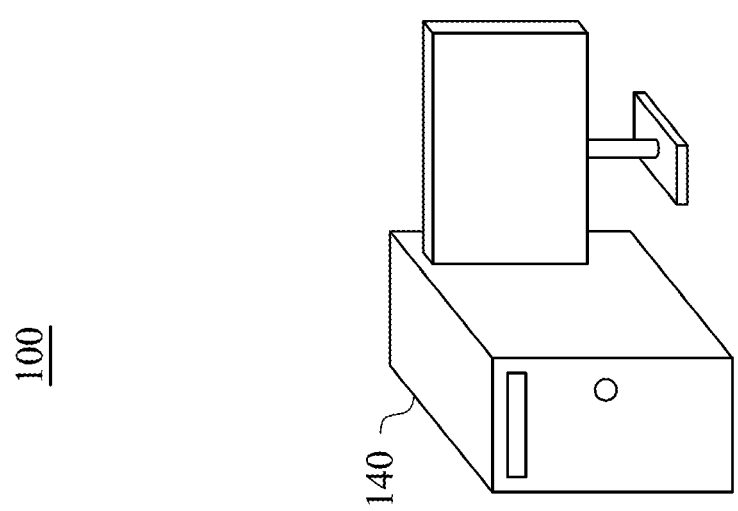

FIG. 1 is a schematic diagram of a system for registering operating images in accordance with an embodiment. Referring to FIG. 1, a system 100 includes an X-ray imaging machine 110, a visible-light camera 120, a rectifier 130, and a computer system 140.

In the embodiment, the X-ray imaging machine 110 is a C-arm X-ray machine which includes an emitting terminal 112 and a receiving terminal 111. The visible-light camera 120 is disposed on the receiving terminal 111.

The visible-light camera 120 may include a Charge-Coupled Device (CCD) sensor, a Complementary Metal- Oxide Semiconductor (CMOS) sensor or other suitable optical sensors. In some embodiment, the visible-light camera 120 may also include an infrared transmitter, an infrared sensor, dual cameras, a structured light sensing device or any device that can sense the depth of the scene.

The computer system 140 is communicatively connected to the X-ray imaging machine 110 and visible-light camera 120 by any wire or wireless communication means. The rectifier 130 can be imaged in an X-ray image. For example, the rectifier 130 includes multiple metal balls 131. X-ray images and visible-light images are combined herein to provide a navigation interface for surgery. Therefore, a coordinate system of the X-ray imaging machine 110 has to be matched to a coordinate system of the visible-light camera 120.

Figure 2:
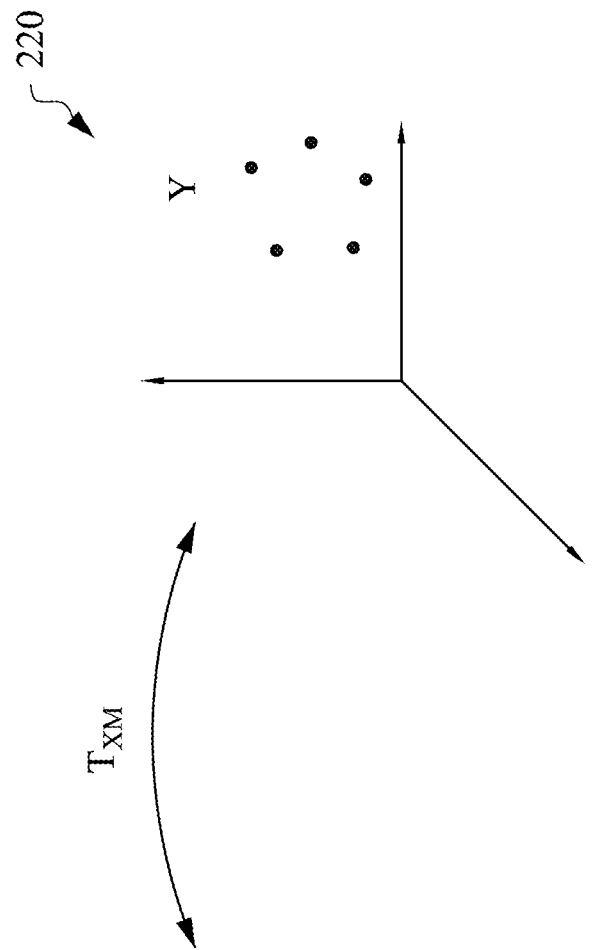
FIG. 2 is a schematic diagram of different coordinate systems in accordance with an embodiment.
Figure 2:
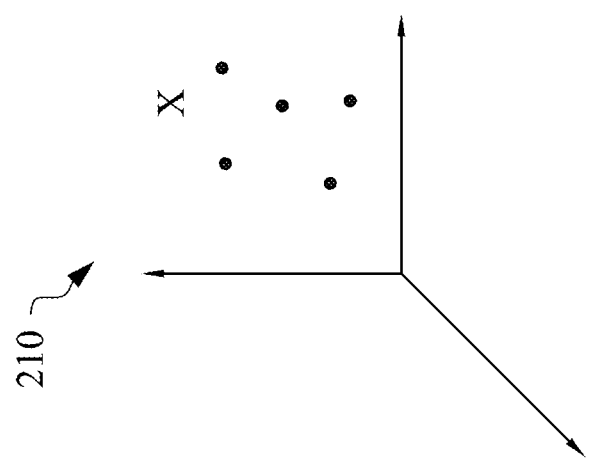

First, the X-ray imaging machine 110 captures a first X-ray image of the rectifier 130, and the visible-light camera 120 captures a first visible-light image of the rectifier 130 at the same time. The computer system 140 can recognize the rectifier 130 in the first X-ray image and in the first visible-light image by any image processing algorithm and computer vision approach. For example, the shape of the rectifier 130 is known, and therefore, the computer system 140 can search the rectifier 130 in the first X-ray image and the first visible-light image based on a preset pattern. After recognizing the rectifier 130, a conversion model between a coordinate system (also referred to as a first coordinate system) of the X-ray imaging machine 110 and a coordinate system (also referred to as a second coordinate system) of the visible-light camera 120 is generated. To be specific, referring to FIG. 2, coordinates of each metal ball 131 in the first coordinate system 210 are represented as a vector X. On the other hand, coordinates of each metal ball 131 in the second coordinate system 220 are represented as a vector Y. After matching the vectors X with the vectors Y, the conversion model is computed according to the following equation (2) in which the conversion model is a matrix $T_{XM}$.

$$X = T_{XM} Y \qquad (2)$$

Figure 3:
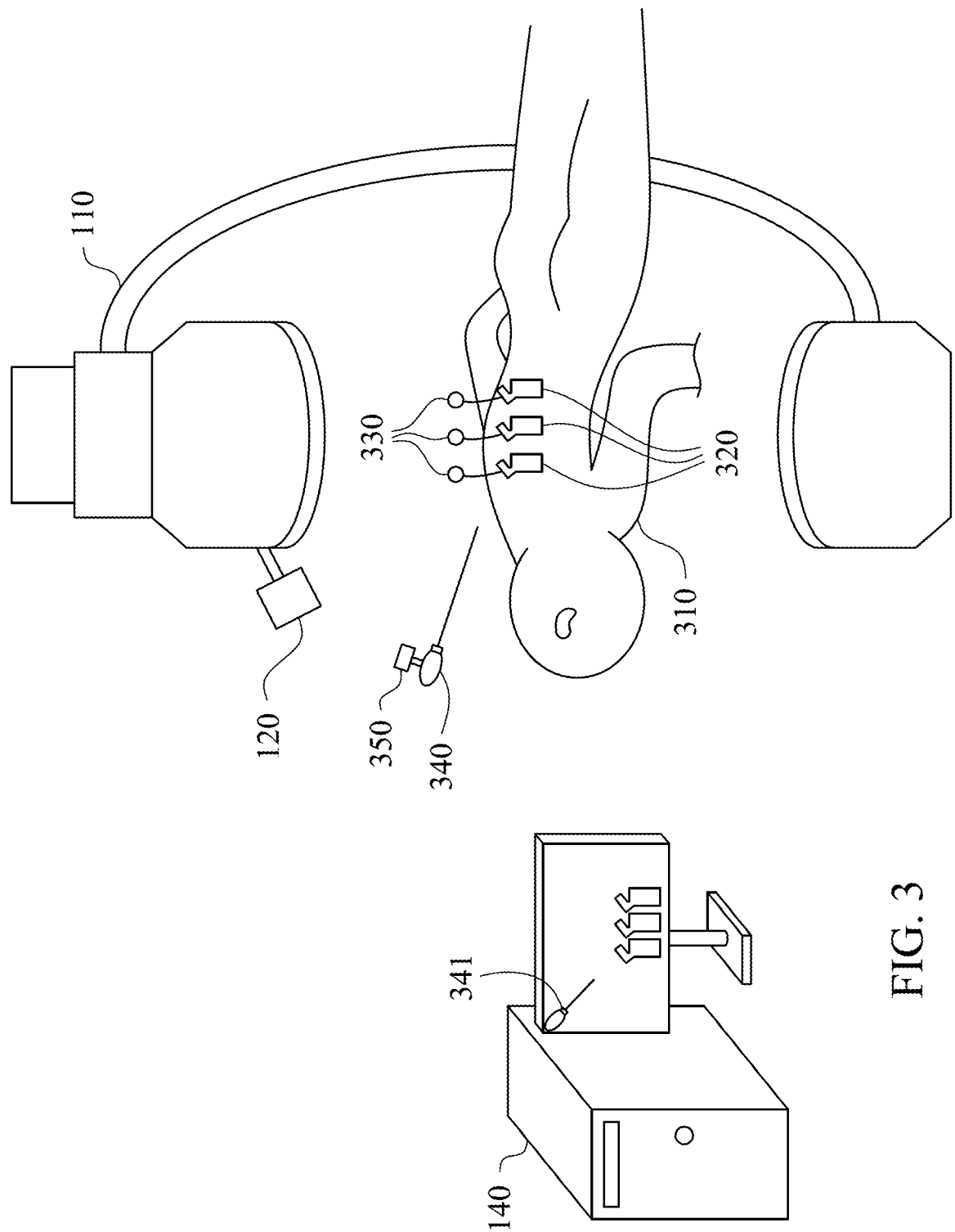
FIG. 3 is a schematic diagram of a system for registering operating images in accordance with an embodiment.

Referring to FIG. 3, after the conversion model is computed, the X-ray imaging machine 110 captures a second X-ray image of a patient 310 on which a positioning mark 330 is set. The positioning mark 330 has special pattern to be recognized. In the embodiment, the doctor intends to perform surgery to the patient's spine, and therefore the positioning mark 330 is disposed on the patient's vertebra 320. The position of the positioning mark 330 changes along with the patient's posture. In other embodiments, the positioning mark 330 may be disposed on another body portion which is not limited in the disclosure.

The visible-light camera 120 captures a second visible-light image of the positioning mark 330. Note that X-ray is harmful, and therefore X-ray images cannot be captured frequently. In the embodiment, images of the positioning mark 330 are captured by the visible-light camera 120, and the position of the vertebra 320 is computed by recognizing the positioning mark 330 in the images.

Next, the computer system 140 combines the second X-ray image and the second visible-light image to provide a navigation interface based on the conversion model (i.e. the matrix $T_{XM}$). In the embodiment, the navigation interface may be shown on the screen of the computer system, but it may be shown on any head mounted device, tablet, or transparent display in other embodiments. Any suitable technology of virtual reality, augmented reality, alternative reality or mixed reality can be used to generate the navigation interface. For example, the spine in the second X-ray image can be divided as vertebras to generate corresponding virtual objects based on an image processing algorithm. The computer system 140 can recognize the positioning mark 330 in the second visible-light image to compute the position of the positioning mark 330, and accordingly renders the corresponding virtual object in the navigation interface. As a result, the doctor can see the position of the vertebra through the navigation interface. In some embodiments, the computer system can transform coordinates of the positioning mark 330 in the second visible-light image into coordinates in the second X-ray image based on the matrix $T_{XM}$, and accordingly make appropriate operations such as segmentation, deformation, scaling, and displacement to at least a portion of the second X-ray image. The processed second X-ray image can be rendered in the navigation interface to reflect the real position of the vertebras.

In some embodiments, the system also includes a surgical instrument 340 and an instrument camera 350 which is fixed on the surgical instrument 340. For example, the surgical instrument 340 includes drills, files, scrapers, saws, screwdrivers or other tools that are commonly used in surgical operations to repair or remove parts of an anatomical area by drilling, grinding, cutting or scraping. The instrument camera 350 may include a CCD sensor, a CMOS sensor or other suitable optical sensors. In some embodiments, the instrument camera 350 may include an infrared transmitter, an infrared sensor, dual cameras, a structured light sensing device or any device that can sense the depth of the scene. The instrument camera 350 captures an image of the positioning mark 330. A conversion model between a third coordinate system of the instrument camera 350 and the second coordinate system is computed by calibration in advance. Therefore, a virtual object 341 of the surgical instrument 340 can be rendered in the navigation interface. The doctor can see the position of the surgical instrument 340 relative to the vertebra through the navigation interface.

Figure 4:
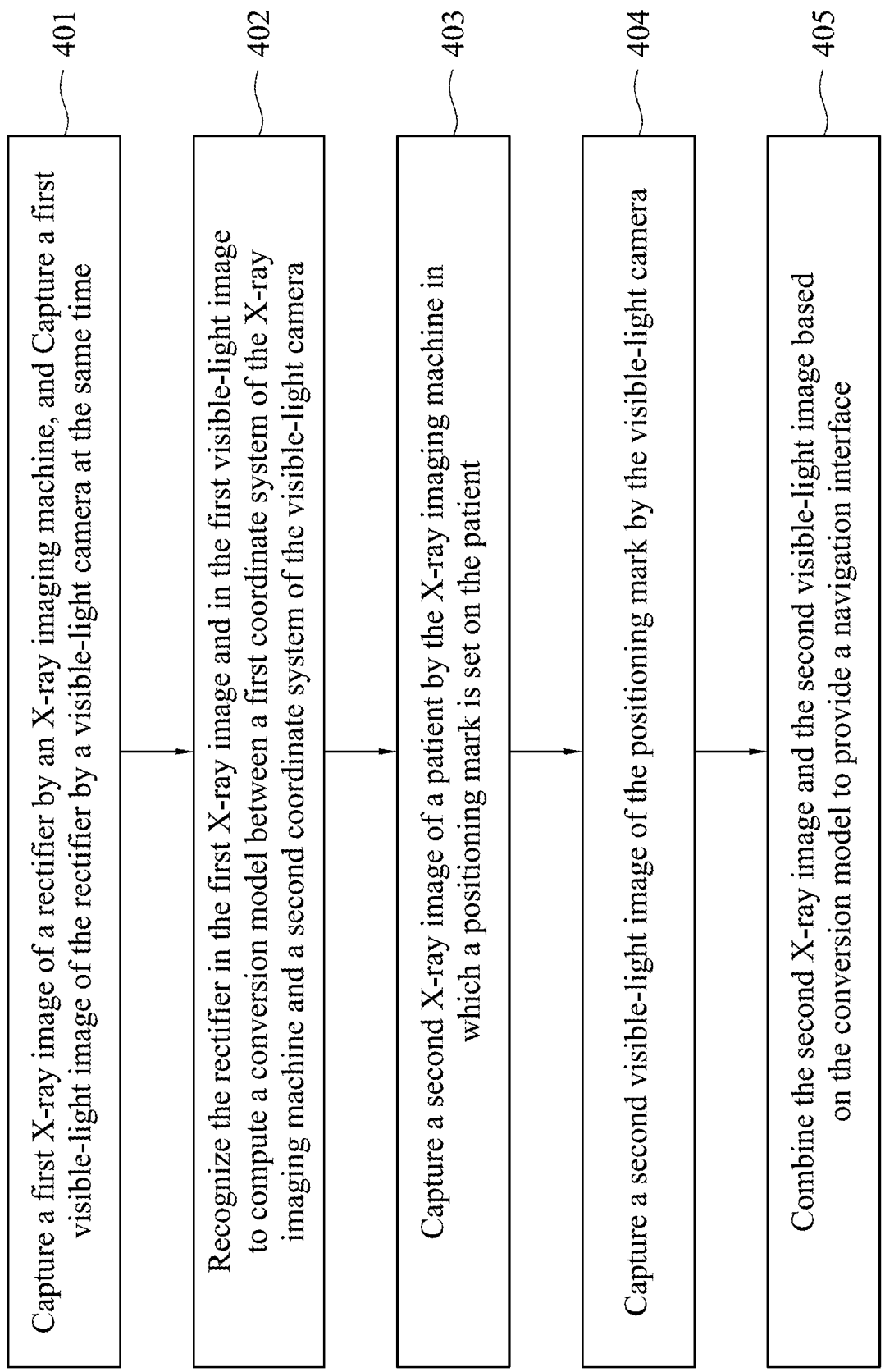
FIG. 4 is a flow chart of a method for registering operating images in accordance with an embodiment.

FIG. 4 is a flow chart of a method for registering operating images in accordance with an embodiment. Referring to FIG. 4, in step 401, a first X-ray image of a rectifier is captured by an X-ray imaging machine, and a first visible-light image of the rectifier is captured by a visible-light camera at the same time. In step 402, the rectifier in the first X-ray image and in the first visible-light image is recognized to compute a conversion model between a first coordinate system of the X-ray imaging machine and a second coordinate system of the visible-light camera. In step 403, a second X-ray image of a patient is captured by the X-ray imaging machine in which a positioning mark is set on the patient. In 404, a second visible-light image of the positioning mark is captured by the visible-light camera. In step 405, the second X-ray image and the second visible-light image are combined based on the conversion model to provide a navigation interface. However, all the steps in FIG. 4 have been described in detail above, and therefore the description will not be repeated. Note that the steps in FIG. 4 can be implemented as program codes or circuits, and the disclosure is not limited thereto. In addition, the method in FIG. 4 can be performed with the aforementioned embodiments, or can be performed independently. In other words, other steps may be inserted between the steps of the FIG. 4.

In the aforementioned embodiments, the system is simplified by disposing the visible-light camera on the X-ray imaging machine. The conversion model between the X-ray imaging machine and the visible-light camera is computed by a rectifier such that the X-ray images and the visible-light images are combined to provide the navigation interface.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A system for registering operating images, the system comprising:
    an X-ray imaging machine;
    a visible-light camera disposed on the X-ray imaging machine;
    a visible marker, wherein the X-ray imaging machine is configured to capture a first X-ray image of the visible marker, and the visible-light camera is configured to capture a first visible-light image of the visible marker at same time; and
    a computer system configured to recognize the visible marker in the first X-ray image and in the first visible-light image to compote a conversion model between a first coordinate system of the X-ray imaging machine and a second coordinate system of the visible-light camera,
    wherein the X-ray imaging machine is further configured to capture a second X-ray image of a patient on which a positioning mark is set, and the visible-light camera is configured to capture a second visible-light image of the positioning mark, wherein the second X-ray image is scanned on the patient with the positioning mark is set on, wherein the conversion model is a matrix, wherein the computer system is configured to transform coordinates of the positioning mark in the second visible-light image into coordinates in the second X-ray image based on the matrix,
    wherein the computer system is configured to provide a navigation interface by combining the second X-ray image and the second visible-light image based on the conversion model,
    wherein the visible marker comprises a pentagon shape with a plurality of metal balls.

2. The system of claim 1, wherein coordinates of the visible marker in the first coordinate system are represented as a vector X, coordinates of the visible marker in the second coordinate system are represented as a vector Y, and the computer system is configured to compute the conversion model according to an equation (1), $$X = T_{XM} Y \qquad (1)$$

wherein the conversion model is the matrix $T_{XM}$.

3. The system of claim 1, wherein the X-ray imaging machine is a C-arm X-ray machine which comprises an emitting terminal and a receiving terminal, and the visible-light camera is disposed on the receiving terminal.

4. The system of claim 1, further comprising a surgical instrument and an instrument camera which is fixed on the surgical instrument.

5. A method for registering operating images for a computer system, the method comprising:
    capturing, by an X-ray imaging machine, a first X-ray image of a visible marker, and capturing, by a visible-light camera, a first visible-light image of the visible marker at same time, wherein the visible-light camera is disposed on the X-ray imaging machine;
    recognizing the visible marker in the first X-ray image and in the first visible-light image to compote a conversion model between a first coordinate system of the X-ray imaging machine and a second coordinate system of the visible-light camera;
    capturing, by the X-ray imaging machine, a second X-ray image of a patient on which a positioning mark is set;
    capturing, by the visible-light camera, a second visible-light image of the positioning mark, wherein the second X-ray image is scanned on the patient with the positioning mark is set on, wherein the conversion model is a matrix, wherein coordinates of the positioning mark in the second visible-light image is transformed into coordinates in the second X-ray image based on the matrix; and
    providing a navigation interface by combining the second X-ray image and the second visible-light image based on the conversion model,
    wherein the visible marker comprises a pentagon shape with a plurality of metal balls.

6. The method of claim 5, wherein coordinates of the visible marker in the first coordinate system are represented as a vector X, coordinates of the visible marker in the second coordinate system are represented as a vector Y, and the method further comprises:
    computing the conversion model according to an equation (1):

$$X = T_{XM} Y \qquad (1)$$

wherein the conversion model is the matrix $T_{XM}$.

7. The method of claim 5, wherein the X-ray imaging machine is a C-arm X-ray machine which comprises an emitting terminal and a receiving terminal, and the visible-light camera is disposed on the receiving terminal.

* * * * *